United States Patent [19]

Martin et al.

[11] Patent Number: 4,702,194
[45] Date of Patent: Oct. 27, 1987

[54] FINGERPRINT CARD HOLDER

[75] Inventors: Timothy S. Martin, Los Angeles; Douglas C. Arndt, Thousand Oaks, both of Calif.

[73] Assignee: Identicator Corp., San Bruno, Calif.

[21] Appl. No.: 866,358

[22] Filed: May 23, 1986

[51] Int. Cl.[4] .......................... B05C 13/02; B41K 1/00
[52] U.S. Cl. .................................... 118/31.5; 118/503
[58] Field of Search .................... 118/31.5, 503; 427/1

[56] References Cited

U.S. PATENT DOCUMENTS

| | | | |
|---|---|---|---|
| 845,624 | 2/1907 | Evans | 118/503 |
| 1,719,950 | 7/1929 | Waggener | 118/503 |
| 2,153,684 | 4/1939 | Ballard | 118/31.5 |
| 4,262,623 | 4/1981 | Smith, III et al. | 427/1 X |

Primary Examiner—John P. McIntosh
Attorney, Agent, or Firm—Jackson & Jones

[57] ABSTRACT

A fingerprint card holder includes a body member defining a flat support surface and a front, back and side walls extending downwardly therefrom. A front guide bar is carried by the body member and extends outwardly from the front wall a distance sufficient to accommodate a fingerprint card so that the card can be inserted between the guide bar and the front wall and then bent back against the support surface to expose a desired row of fingerprint receiving spaces. The guide bar includes inwardly extending studs which are biased against the front wall to hold the card while it is being bent. A releasable adhesive is secured to the support surface to releasably hold a card thereagainst.

1 Claim, 6 Drawing Figures

U.S. Patent  Oct. 27, 1987  4,702,194
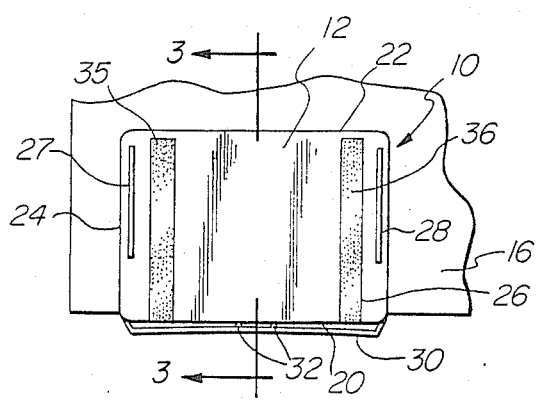
FIG. 1
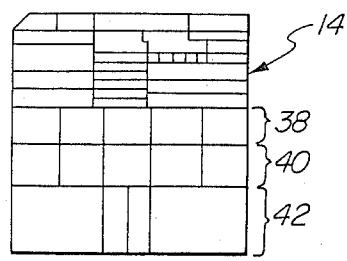
FIG. 2
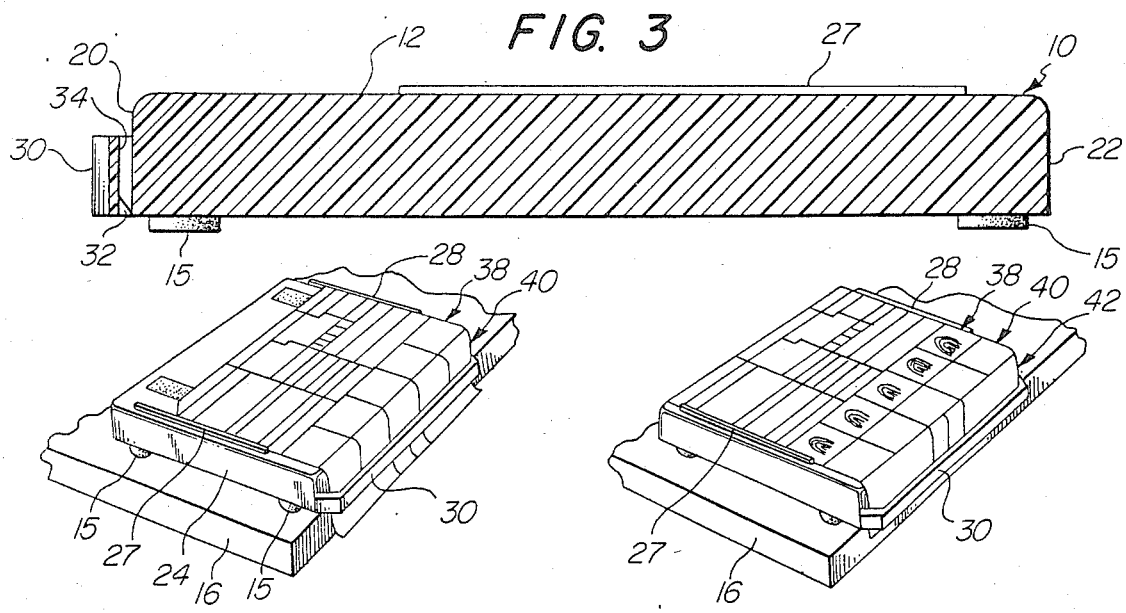
FIG. 3
FIG. 4
FIG. 5
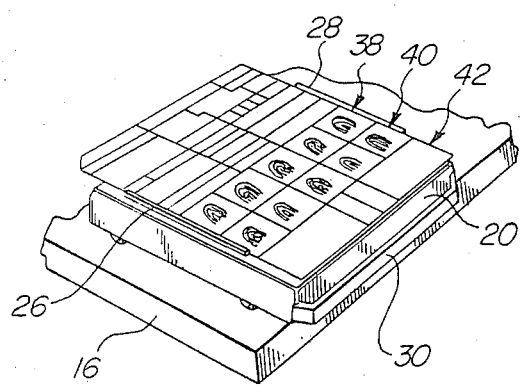
FIG. 6

FINGERPRINT CARD HOLDER

BACKGROUND OF THE INVENTION

1. Field of the Invention

The present invention is directed to fingerprint card holders and, more particularly, to a card holder which allows the card to be bent so that rows of prints can be placed on the card successively without disturbing the spaces for prints contained in other rows.

2. Description of the Prior Art

The art of fingerprinting and identifying persons by their fingerprints is well known. Both ink and inkless methods of taking a person's fingerprints are in widespread use. Either a colored ink or a colorless reagent is applied to the persons fingertips and subsequently the fingers are rolled (or pressed) onto a clean recording surface, such as paper, to deposit the ink or reagent on the surface in a pattern corresponding to the fingerprints. In the inkless method, an additional chemical or reagent is applied to the surface to develop the print so that it is visible. See, for example, U.S. Pat. No. 4,262,623 assigned to the assignee of the present application.

Fingerprint cards have been standardized by many governmental agencies such as the U.S. Federal Bureau of Investigation. Such standardized cards are of uniform size i.e. 8"×8" and are arranged with separate rows of spaces for the individual prints of each hand and a bottom row for the prints of the thumbs and the four fingers of each hand taken simultaneously.

To take a person's fingerprints the cards have generally been placed on a table or the like. This has often resulted in movement of the card while the prints are being taken with the result that the prints become smudged. Small boardds designed to rest on a table have also been used in which an adhesive is carried on the board to releasably hold the card flat against the board. While the adhesive prevents the card from moving relative to the board and thereby aids in preventing smudging during the fingerprint process, it does not prevent the fingerprint chemicals such as ink from being accidently transferred from the person's hand to spaces reserved for prints of fingers not being taken at that time. To provide clear legible prints it is important to eliminate smudging and the transfer of chemicals to spaces not receiving prints.

U.S. Pat. No. 4,262,623 ('623), assigned to the assignee of this application, discloses a fingerprinting device having a flat surface for receiving a card and a pivotably mounted lever designed to engage the card at its edges and hold it against the flat surface. A portion of the card can be bent down to expose the top row or rows of spaces at a time. Other prior art card holders function in a similar manner. While the card holder portion of device of the '623 patent is an improvement over the prior art, it is expensive and somewhat difficult to use. There is still a need for a simple, reliable and inexpensive fingerprint card holder.

SUMMARY OF THE INVENTION

In accordance with the present invention, a fingerprint card holder is provided which includes a body member adopted to rest on a flat surface such as a table. The body member defines a flat support surface on the top thereof, and includes means for positioning the support surface above the flat surface. A front wall extends downwardly from the support surface and a front guide member is spaced from and extends outwardly from the front wall to allow the card to be inserted between the guide and the front wall. The guide includes at least one stud spaced on either side of the center thereof. The studs extend toward the front wall. The central portion of the member is guide biased toward the front wall so that the studs will releasably hold a card against the front wall. An adhesive is secured to the support surface and arranged to releasably hold the card against the support surface when the card is pressed thereagainst whereby the card may be inserted between the guide and front wall of the holder and then bent back against the support surface to align a desired row of fingerprint spaces at the front of the body member. In the preferred embodiment, the body member is further provided with guide rails extending upwardly from the support surface and spaced apart to accommodate a fingerprint card therebetween.

BRIEF DESCRIPTION OF THE DRAWINGS

FIG. 1 is plan view of a fingerprint card holder in accordance with the present invention;

FIG. 2 is a plan view of a standard fingerprint card;

FIG. 3 is a cross-sectional view of the card holder of FIG. 1 taken along lines 3—3;

FIG. 4 is a perspective view of the card holder of FIG. 1 showing a fingerprint card releasably secured thereto so that the upper row of spaces for receiving fingerprint is positioned along the front edge of the holder;

FIG. 5 is another perspective view of the card holder of FIG. 1 holding a card so that the second row of fingerprint spaces is positioned along the front edge; and FIG. 6 is yet another perspective view of the card holder of FIG. 1 holding a card so that the third row of fingerpring spaces is positioned along the front edge.

DESCRIPTION OF THE PREFERRED EMBODIMENT

The following specificaiton taken in conjunction with the accompanying drawings sets forth the preferred embodiment of the present invention. This embodiment is the best mode contemplated by the inventors for carrying out their invention, although it should be understood that various modifications can be made without departing from the spirit and scope of the invention.

Referring now to FIGS. 1 through 3, the card holder includes a body member 10 which defines a flat support surface 12 for receiving and supporting a fingerprint card 14 (shown in FIG. 2) as will be explained. Four stubby legs or feet 15 position the support surface 12 above a table 16 or the like. The body member 10 defines front, back and side walls 20, 22, 24 and 26 extending downwardly from the support surface as illustrated. A pair of parallel side rails 27 and 28 extend upwardly from the support surface 12 and are spaced apart to accommodate the fingerprint card 14 therebetween.

A front guide member or bar 30 is molded integrally with the body member 10 and is spaced from and extends outwardly from the front wall 20 to allow a fingerprint card to be inserted between the guide bar 30 and front wall 20. A pair of holding studs 32 in the form triangular spikes extend from the inner wall 34 of the guide bar toward the front wall. The guide bar 30 functions as a spring with the central portion, which carries the studs 32, biased against the front wall 20 so that the studs pin the card 14 against the front wall 20 when the card has been inserted between the front wall 20 and the guide bar 30.

Two parallel strips 35 and 36 of releasable adhesive are affixed to the support surface 12 with one strip 14 extending adjacent the side rail 27 and the other extending near the side rail 28 as shown. The adhesive strips are preferably in the form of double coated tape with a high strength adhesive on one side and a low strength adhesive on the other. The high strength adhesive side is affixed to the support surface and the low strength adhesive remains on the side which receives the card so that the cards can be removed from the support surface without defacing the card.

Referring now to FIG. 2, the card 14 is conventionally made of a heavy paper and contains three rows of prearranged areas or spaces 38, 40 and 42 for receiving fingerprints. Rows 38 and 40 are arranged to receive the prints of the right and left hand fingers, respectively, and row 42 is arranged to receive the prints of all four fingers and the thumb of each hand as is well known in the art. The spaces above row 38 are designed to have personal identification information typed or written thereon.

To use the fingerprint card holder of this invention, an operator initially places the holder near the edge of a flat surface of suitable height such as provided by the table 16. The operator then takes a fingerprint card such as the card 14 and inserts the bottom end thereof between the guide 30 and the front wall 20 until the desired row (e.g. 38) of spaces is positioned just above the front edge or wall 20 of the holder. The top of the card is then bent down against the support surface 12 and the adhesive strips 35 and 36. Fingerprints are applied to the spaces in that row, and the top of the card is then lifted off of the support surface and the process repeated until all desired rows of spaces are filled with prints. See FIGS. 5 and 6. The card is then removed and the process repeated for a new card.

There has been described an improved fingerprint card holder which is simple, inexpensive and efficient use. The holder prevent the card from moving during the fingerprinting process and enables the user to prevent fingerprint chemicals from being inadvertently deposited on spaces reserved for prints of fingers not being taken.

The above description presents the best mode contemplated in carrying out our invention. Our invention is, however, susceptible to modifications and alternate constructions from the embodiments shown in the drawings described above. Consequently, it is not the intention to limit the invention to the particular embodiment disclosed. On the contrary, the invention is intended and shall cover all modifications, sizes and alternate constructions falling within the spirit and scope of the invention, as expressed in the appended claims when read in light of the description and drawings.

What is claimed is

1. A fingerprint card holder which comprises:

a body member adapted to rest on a flat surface and defining a flat support surface on the top thereof, a front wall, a back wall, and a pair of parallel side walls extending downwardly from the top surface, the body member further defining a pair of upstanding side guide rails extending parallel to the side walls and spaced apart to accommodate a fingerprint card therebetween, the support surface and the side guide rails being arranged to allow the card to be placed on the support surface from a position above said surface;

an elongated front guide member secured to the body member and defining a guide surface extending parallel to the front wall of the body member and spaced therefrom to accommodate a fingerprint card inserted between the front wall and the guide surface, the front guide member including at least two spaced studs extending from the central portion of the guide surface toward the front wall of the body member, the center portion of the guide member being biased toward the front wall so that a card inserted between the guide surface and the front wall of the body member will be held against the front wall by the studs while the portion of the card extendign above the support surface is being bent backwardly to lie flat against the support surface; and a strip of adhesive extending along the support surface of the body member in a direction perpendicular to the front wall and adjacent each side guide rail, the adhesive material having a high adhesive strength on the side engaging the support surface and a low adhesive strength on the other side releasably holding the card flat against the support surface.

* * * * *